(12) United States Patent
Pastron

(10) Patent No.: US 7,827,985 B2
(45) Date of Patent: Nov. 9, 2010

(54) INSERTION AID FOR ORAL AND NASAL MEDICAL DEVICES

(75) Inventor: Nick Pastron, Long Island City, NY (US)

(73) Assignee: ABL IP Holding LLC, Conyers, GA (US)

( * ) Notice: Subject to any disclaimer, the term of this patent is extended or adjusted under 35 U.S.C. 154(b) by 929 days.

(21) Appl. No.: 11/415,324

(22) Filed: May 1, 2006

(65) Prior Publication Data

US 2007/0272258 A1 Nov. 29, 2007

(51) Int. Cl.
*A61M 16/00* (2006.01)

(52) U.S. Cl. .............. 128/200.26; 128/200.24; 128/207.14

(58) Field of Classification Search ............ 128/200.26, 128/203.13, 205.19, 206.11, 860, 200.15, 128/200.24, 206.29, 207.14; 433/91–95; 604/19, 35, 77, 118–121, 275–279; 600/240, 600/241, 185–200; D24/136
See application file for complete search history.

(56) References Cited

U.S. PATENT DOCUMENTS

| | | | | |
|---|---|---|---|---|
| 1,613,373 A * | 1/1927 | Beck | ........................... | 600/205 |
| 4,306,547 A * | 12/1981 | Lowell | ...................... | 600/188 |
| 4,802,851 A * | 2/1989 | Rhoades | ...................... | 433/93 |
| 4,883,426 A * | 11/1989 | Ferrer | ......................... | 433/91 |
| 4,982,729 A * | 1/1991 | Wu | ............................. | 600/187 |
| 5,394,865 A * | 3/1995 | Salerno | ...................... | 600/199 |
| 6,176,824 B1 * | 1/2001 | Davis | ......................... | 600/178 |
| 2004/0019256 A1 * | 1/2004 | Cubb et al. | ................. | 600/188 |
| 2005/0065411 A1 * | 3/2005 | Baldwin et al. | ............. | 600/240 |
| 2005/0240081 A1 * | 10/2005 | Eliachar | ..................... | 600/199 |
| 2006/0036133 A1 * | 2/2006 | Demsky | ..................... | 600/240 |
| 2006/0065268 A1 * | 3/2006 | Koyama et al. | ......... | 128/200.26 |
| 2007/0093693 A1 * | 4/2007 | Geist et al. | ................... | 600/199 |

* cited by examiner

*Primary Examiner*—Justine R Yu
*Assistant Examiner*—Rachel T Young
(74) *Attorney, Agent, or Firm*—Kilpatrick Stockton LLP

(57) ABSTRACT

An insertion aid device includes a handle to hold the insertion aid device and a tongue depressor to depress the tongue of the patient. A curved wedge-shaped tongue depressor maintains the patient's mouth in an open position.

14 Claims, 3 Drawing Sheets

INSERTION AID FOR ORAL AND NASAL MEDICAL DEVICES

FIELD OF THE INVENTION

The present multipurpose invention relates to a method and apparatus for uncoiling Nasogastric tubes within the mouth during insertion, maintaining the patient's mouth in an open position for Orogastric tube insertion and oral cleaning/suctioning and more particularly for inserting tracheal suctioning catheters for tracheal suctioning of secretions which are causing difficulties in breathing and causing certain types of the pneumonia.

BACKGROUND OF THE INVENTION

Oral cleaning/suctioning instruments and tracheal suctioning catheters are commonly used in health care patients with respiratory distress, critical illness, chronic illness, terminal illness, weakness, paralysis or any patient requiring breathing support from a ventilator. Patients are usually in an altered mental state from sedation, confusion or being frightened and sometimes do not cooperate for oral cleaning/suctioning and tracheal suctioning. Patients sometimes bite down on the cleaning and suctioning instruments and sometimes break a piece of the instrument off in the mouth or even bite caregivers fingers. Other problems that exist is a spread of bacteria from the mouth to the lungs when tracheal suctioning and instrument insertion trauma to the nose or mouth. Nasogastric tubes and orogastric tubes are commonly used in the course of health-care, most frequently in the preparation before, during and after surgery. The nasogastric and orogastric tubes have been a problem for patients and clinicians for some time. When the nasogastric tubes are inserted into the nose, sometimes these tubes coil in the back of the throat. When inserting orogastric tubes, patients tend to bite down and stop the process. There is also the danger of the patient biting the caregiver's finger. Typically, these nasogastric/orogastric tubes are formed from the resilient plastic material such as polyurethane polyethylene or silicone polymer. These tubes typically have a proximal end, a distal and a central lumen or passageway. Further details about such tubes can be found in the U.S. Pat. Nos. 4,778,448 and 4,634,425 the disclosures of which are incorporated herein by reference. These tubes may be manufactured from surgical steel additionally.

SUMMARY OF THE INVENTION

The insertion aid system for oral and nasal medical devices is a medical instrument that may be used by doctors, nurses and other caregivers. The device of the present invention may be formed from metal or plastic or any such other suitable material to allow the doctors, nurses and other caregivers to guide and insert these oral and nasal instruments in patient's throat or down the throat or nose with greater ease both to the patient and medical technician.

The insertion aid system for oral and nasal medical devices is advanced into the oral cavity, depressing the patient's tongue and maintaining the patient's mouth in the open position therefore oral cleaning/suctioning and orogastric tube insertion is made easily. If tracheal suctioning is desired, a suction catheter can be advanced through the suction catheter guide directly to the back of the throat and down the trachea to suction of secretions that the patient is unable to cough up.

Most patients independent of their age, young or old, have difficulty with these types of instruments being inserted down the nose or throat. The teachings of the present invention eliminates the coiling of these instruments, eliminates the finger bite injury to the caregiver, prevents the patient from biting down on or possibly breaking instruments in the oral cavity and decreases the risk of introducing oral bacteria in the lungs.

The device will include a light and switch for providing light so that the caregiver can see into the oral cavity and throat of the patient.

BRIEF DESCRIPTION OF THE DRAWINGS

The invention may be understood by reference to the following description taken in conjunction with the accompanying drawings, in which, like reference numerals identify like elements, and in which.

DETAILED DESCRIPTION

Figure 1:
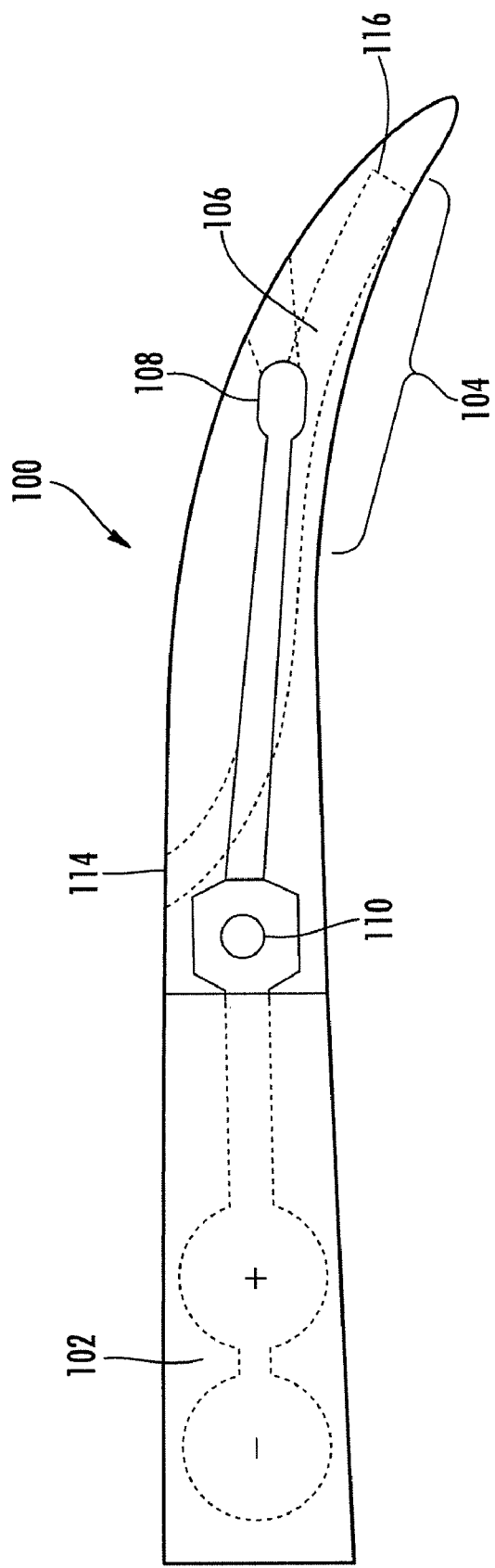
FIG. 1 illustrates a cross-sectional view of the insertion aid device of the present invention.

FIG. 1 illustrates the insertion aid device 100 which includes a handle 102 which may have a circular cross-section and which may be constructed of rigid material such as plastic or steel or any other suitable material. The handle 102 may include a textured surface to prevent the insertion aid device 100 from slipping.

The insertion aid device 100 includes a curved tongue depressor 104 which is connected to the handle 102 and which includes an declining surface to aid in the depression of the tongue and to aid in the insertion of the insertion aid device 100. The curved tongue depressor 104 has a progressive reducing diameter which becomes increasingly smaller in the direction of the distal end. The curved tongue depressor 104 includes a tracheal suction catheter guide 106 to guide a tracheal suction catheter to be inserted into a patient. The tracheal suction catheter guide 106 includes a first opening 114 which is located near the proximal end of the curved tongue depressor 104 for the insertion of the tracheal suction catheter to be inserted into the patient. The tracheal suction catheter guide 106 includes a second opening 116 at the distal end of the curved tongue depressor 104 to provide an exit for the tube to be inserted into the patient. The tracheal suction catheter guide 106 provides for effective suctioning of secretions and prevents the coiling of the tube in the mouth and decreases the triggering of the gag reflex by the patient. Furthermore, the tracheal suction catheter guide 106 prevents the introduction of bacteria into the oral cavity and consequently prevents the introduction of bacteria into the lungs, decreasing the risk of infection. The shape of the curved tongue depressor 104 depresses the tongue and maintains the patient's mouth in an open position, preventing the patient from fighting the user and provides better viewing of the oral cavity, enables proper insertion of the orogastric tube and enhances the oral cleaning and suctioning. The curved tongue depressor 104 may be constructed from rigid material such as plastic or steel or other suitable material.

The curved tongue depressor 104 includes a light 108 formed in the declining surface which may include an integral battery and includes a switch 110 located near the proximal end of the curved tongue depressor 104. The operator of the insertion aid device 100 can activate the light 108 by the switch 110. The light 108 will include a light bulb which may be a conventional light bulb or LED.

The length of the insertion aid device 100 may vary in accordance with the dimensions of the mouth of the patient. For example, the insertion aid device 100 could be manufactured in three sizes, one appropriate for an adult, a second appropriate for a child and a third appropriate for an infant. Typically, the insertion aid device 100 may be between approximately 6 inches long and 12 long. The circumference of the insertion aid device 100 would be based upon the size of the mouth or oral cavity for the intended user for example, an adult, a child or an infant. The length of the handle may be between three and 4 inches.

Figure 2:
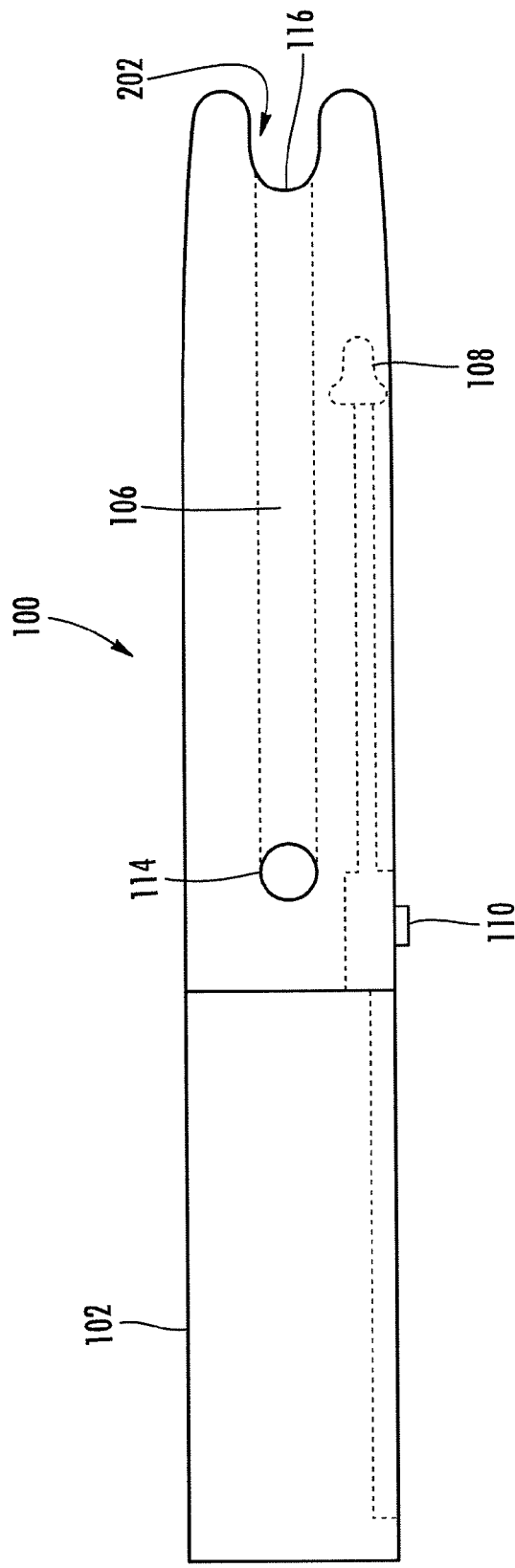
FIG. 2 illustrates a top view of the insertion aid device of the present invention.
Figure 3:
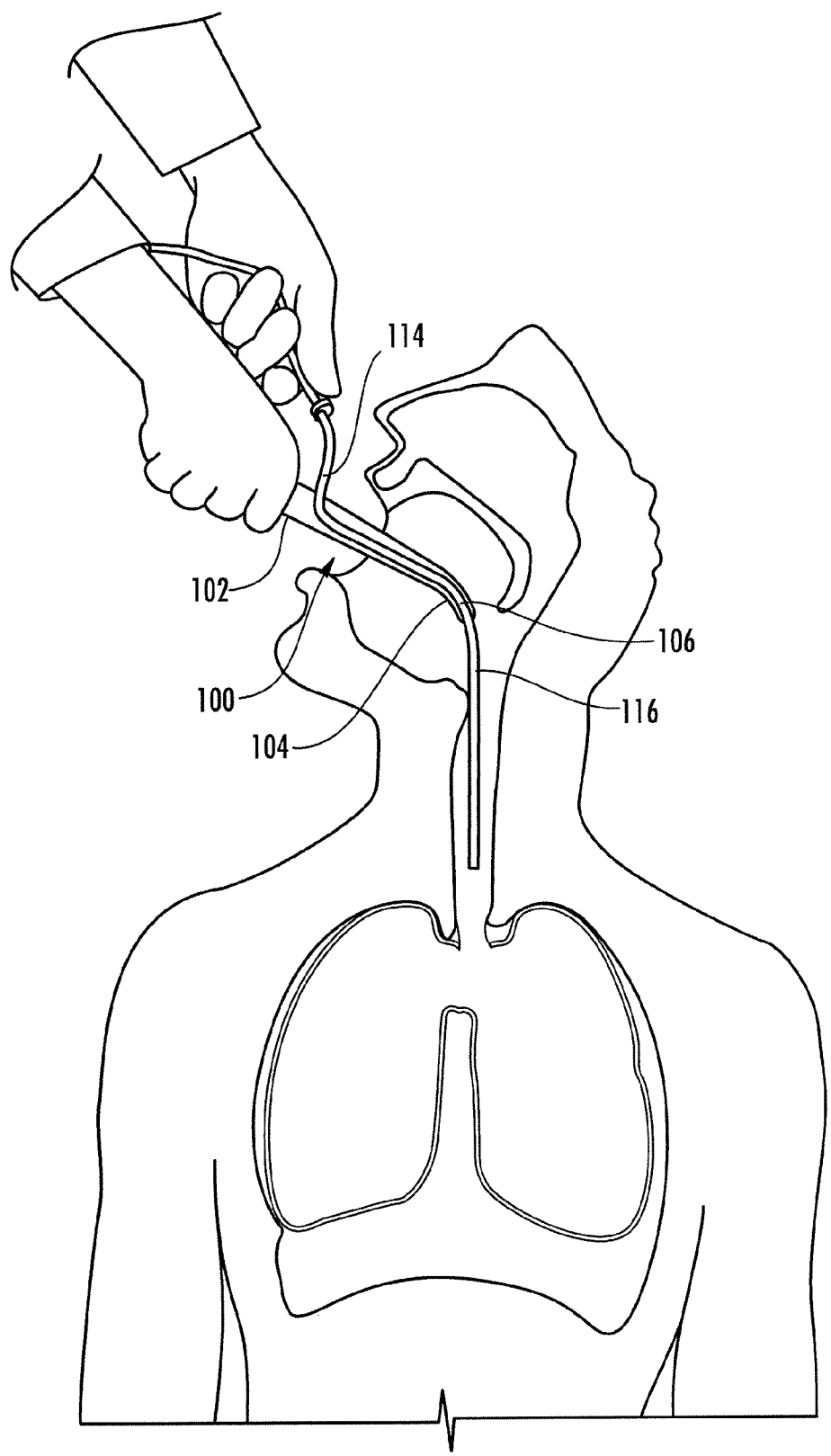
FIG. 3 illustrates a cross-sectional view of the use of the insertion aid device with the patient.

FIG. 2 illustrates a top view of the insertion aid device 100 and shows the switch 110 which controls the operation of a light 108. Additionally shown in FIG. 2 is the tube guide 106 positioned along the longitudinal axis of the insertion aid device 100. A curved edge 202 is positioned at the distal end of the insertion aid device 100 to form a groove that can straighten out a coiled nasogastric tube within the mouth of the patient. The curved edge 202 prevents the coiling of the suction tube within the mouth of the patient and decreases the triggering of the gag reflex.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed.

The invention claimed is:

1. A tracheal suction catheter insertion device, comprising:
    (a) a handle comprising a distal end;
    (b) a tongue depressor comprising:
        (i) an upper surface;
        (ii) a proximal end coupled to the distal end of the handle; and
        (iii) a distal end configured to contact a patient's mouth cavity without entering the patient's throat;
    (c) a tracheal suction catheter guide comprising:
        (i) a first opening adjacent the upper surface and the proximal end of the tongue depressor;
        (ii) a second opening adjacent the distal end of the tongue depressor; and
        (iii) an enclosed channel connecting the first opening to the second opening;
    (d) a light adjacent the upper surface of the tongue depressor; and
    (e) the tongue depressor and the tracheal suction catheter guide comprising a rigid material.

2. An insertion aid device as in claim 1, wherein the handle is textured.

3. An insertion aid device as in claim 1, wherein the handle has a substantially circular cross-section.

4. An insertion aid device as in claim 1, wherein the tongue depressor has a declined surface.

5. An insertion aid device as in claim 1, wherein the tongue depressor has a progressively reduced diameter.

6. An insertion aid device as in claim 1, wherein the tracheal suction catheter guide is configured to prevent coiling of the tracheal suction catheter in use.

7. An insertion aid device as in claim 1, wherein the tracheal suction catheter guide is configured to prevent a patient from biting down on the tracheal suction catheter in use.

8. An insertion aid device as in claim 1, wherein the tongue depressor includes a curved edge.

9. An insertion aid device as in claim 1, wherein the curved edge is located at a distal end of said tongue depressor.

10. An insertion aid device as in claim 1, wherein the light includes an integral battery.

11. An insertion aid device as in claim 1, wherein the light is a LED light.

12. An insertion aid device as in claim 1, wherein the tongue depressor includes a switch to control the light.

13. An insertion aid device as in claim 1, wherein the light is positioned at a distal end of the tongue depressor.

14. An insertion aid device as in claim 12, wherein the switch is positioned at a proximal end of the tongue depressor.

\* \* \* \* \*

UNITED STATES PATENT AND TRADEMARK OFFICE
CERTIFICATE OF CORRECTION

PATENT NO. : 7,827,985 B2　　　　　　　　　　　　　　　　　　　　　Page 1 of 1
APPLICATION NO. : 11/415324
DATED : November 9, 2010
INVENTOR(S) : Nick Pastron It is certified that error appears in the above-identified patent and that said Letters Patent is hereby corrected as shown below:

Title Page, please delete the following assignee data:

"(73) Assignee:  ABL IP Holding LLC, Conyers, GA
                 (US)"

Signed and Sealed this
Thirty-first Day of May, 2011

David J. Kappos
*Director of the United States Patent and Trademark Office*